(12) United States Patent
Kanji et al.

(10) Patent No.: US 6,726,917 B2
(45) Date of Patent: Apr. 27, 2004

(54) FIBER-CONTAINING COSMETIC COMPOSITION

(75) Inventors: Mohamed Kanji, Edison, NJ (US); Ewelina Pitusiak, Union, NJ (US)

(73) Assignee: L'Oreal SA, Paris (FR)

( * ) Notice: Subject to any disclaimer, the term of this patent is extended or adjusted under 35 U.S.C. 154(b) by 0 days.

(21) Appl. No.: 09/737,868

(22) Filed: Dec. 18, 2000

(65) Prior Publication Data

US 2003/0059448 A9 Mar. 27, 2003

(51) Int. Cl.[7] .............. A61K 6/00; A61K 7/00; A61K 7/021; A61K 47/32
(52) U.S. Cl. ............ 424/401; 424/70.7; 424/63; 514/772.4
(58) Field of Search .............. 424/401, 70.7, 424/63; 514/772.4

(56) References Cited

U.S. PATENT DOCUMENTS

| 3,384,547 A | 5/1968 | Palmerio et al. ............ 167/85 |
|---|---|---|
| 4,135,527 A | 1/1979 | Montiel ..................... 132/88.7 |
| 5,534,247 A * | 7/1996 | Franjac et al. ............. 424/70.7 |
| 6,264,933 B1 * | 7/2001 | Bodelin et al. ............ 424/70.7 |

FOREIGN PATENT DOCUMENTS

| JP | 7-267827 | 10/1995 |
|---|---|---|
| JP | 7-267828 * | 10/1995 |
| JP | 10-291917 | 11/1998 |

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

The invention provides a cosmetic composition, particularly useful as a mascara, containing fibers, pigments, and at least two film formers: at least one tacky film former soluble or dispersible in water and at least one tacky film former soluble in oil chosen from hydrogenated polyisobutenes, adipic acid/diethylene glycol/glycerin crosspolymers, polyethylenes, and polyvinyl laurates. The invention also relates to a method for providing volume and/or length to eyelashes using the inventive composition.

51 Claims, No Drawings

FIBER-CONTAINING COSMETIC COMPOSITION

The present invention is directed to cosmetic compositions, such as mascara compositions, containing fibers, at least one pigment, and at least two film formers: at least one tacky film former soluble or dispersible in water and at least one tacky film former soluble in oil chosen from hydrogenated polyisobutenes, adipic acid/diethylene glycol/glycerin crosspolymers, polyethylenes, and polyvinyl laurates. When the inventive mascara is applied to eyelashes, a lengthening effect may be observed.

The use of fibers in mascara compositions to lengthen or volumize eyelashes is known in the art. However, the inclusion of fibers in these compositions has presented various possible difficulties. Primary among the possible drawbacks of fiber use has been undesirable flaking and detachment of the fibers from the eyelashes that may occur due to the insufficient adhesive properties of the film formers in the mascara. Such flaking also may make it difficult to apply more than one coat of mascara, as the application of subsequent coats may further act to detach fibers from the lashes.

Accordingly, there existed a need in the art to find a way to use fibers to obtain enhanced volume and/or length for eyelashes without the disadvantages of flaking and detachment of the fibers. It was also desired to use fibers but also obtain ease of application. Development of such compositions involves a difficult balance, as the tackiness of film formers used in a fiber-containing cosmetic composition, particularly for use on eyelashes, should be enough to prevent the fibers from flaking off over time, but not so tacky that the composition is not easily removable from the eyelashes and is sticky and uncomfortable.

The present invention addresses these issues. Accordingly, the present invention, in one aspect, provides a cosmetic composition comprising fibers, at least one pigment, at least one tacky film former soluble or dispersible in water, and at least one tacky film former soluble in oil chosen from hydrogenated polyisobutenes, adipic acid/diethylene glycol/glycerin crosspolymers, polyethylenes, and polyvinyl laurates. In the inventive mascara, the combination of tacky film formers may allow, in at least some embodiments, one or more of the following to occur: allow the fibers to adhere to the eyelashes, allow optimal water resistance and allow minimal flaking. The invention also relates to a method for providing length and/or volume to eyelashes by applying to the eyelashes a fiber-containing mascara composition as described above.

Reference will now be made in detail to exemplary embodiments of the present invention. The invention, in one aspect, provides a cosmetic composition comprising fibers, at least one pigment, at least one tacky film former soluble or dispersible in water, and at least one tacky film former soluble in oil chosen from hydrogenated polyisobutenes, adipic acid/diethylene glycol/glycerin crosspolymers, polyethylenes, and polyvinyl laurates. In one embodiment, the composition of the invention is used as a mascara. The fibers in the composition may, for example, act to provide length and/or volume to the eyelashes by stably adhering to the eyelashes. More particularly, the specific combination of tacky film formers in the inventive mascara may allow the fibers to adhere to the eyelashes but without being so tacky as to cause the eyelashes to stick or clump together. The composition may also be easy to apply, easy to remove, water-resistant and/or comfortable to wear. For purposes of this invention, "tacky" is defined as sticky or adhesive to the touch.

Also, for purposes of this invention, the term "soluble or dispersible in water" means that the substance in question will not precipitate out or coagulate, i.e., that it dissolves up to the limit of saturation. The term "soluble in oil" means "miscible in oil"; in other words, if a substance is not soluble in oil, it is immiscible, forming distinct layering in the oil phase, an indication that the substance is not compatible or soluble in the oil phase.

The at least one tacky film former soluble or dispersible in water may be chosen from polyvinyl alcohols (such as the AIRVOL series from Air Products); polyvinyl acetates (such as FULATEX (R) sold by H. B. Fuller Co.); cellulose acetate phthalate aqueous dispersions (such as AQUACOAT CPD sold by FMC Corp.); and acrylates copolymers, such as DATTOSOL 5080 AD sold by Kobo Products, vinylpyrrolidone/acrylates/lauryl methacrylate copolymers (such as STYLEZE 2000 sold by ISP), acrylates/$C_{1-2}$ succinates/hydroxyacrylates copolymers (such as ALLIANZ LT-120 sold by ISP), PVP/DMAPA acrylates copolymers (such as STYLEZE CC-10 sold by ISP), and crosslinked poly (2-ethylhexyl acrylates) in water (such as GEL-TAC 100 series sold by API). In one embodiment, the at least one tacky film former soluble or dispersible in water is chosen from an acrylates copolymer and polyvinyl acetates. The at least one tacky film former soluble or dispersible in water may be present in the composition in an amount ranging from 0.5% to 25% relative to the total weight of the composition. In another embodiment, the at least one tacky film former soluble or dispersible in water may be present in an amount ranging from 1% to 15%, relative to the total weight of the composition. In still another embodiment, the at least one tacky film former soluble or dispersible in water may be present in an amount ranging from 1% to 10%, relative to the total weight of the composition.

The at least one tacky film former soluble in oil is chosen from hydrogenated polyisobutenes, adipic acid/diethylene glycol/glycerin crosspolymers (such as that sold as LEX-OREZ 100 by Inolex), polyethylenes, and polyvinyl laurates. In one embodiment, the at least one oil-soluble tacky film former is chosen from hydrogenated polyisobutenes. Hydrogenated polyisobutenes are available from, for example, Collaborative Laboratories, East Setauket, N.Y., under the name POLYSYNLANE. In one embodiment, the hydrogenated polyisobutenes to be used in the claimed invention have a weight average molecular weight of greater than 1500. In another embodiment, the hydrogenated polyisobutenes have a weight average molecular weight greater than 2000 and in yet another embodiment, greater than 3000. The at least one tacky film former soluble in oil may, for example, be present in the composition in an amount ranging from 0.5% to 30%, relative to the total weight of the composition. In one embodiment, the at least one tacky film former soluble in oil is present in the composition in an amount ranging from 1% to 20%, relative to the total weight of the composition. In yet another embodiment, the at least one tacky film former soluble in oil may be present in the composition in an amount ranging from 1% to 15%, relative to the total weight of the composition.

The composition according to the invention may further contain at least one additional film former chosen from the list of film formers set forth on pages 1744–1747 of the CTFA International Cosmetic Ingredient Dictionary, $8^{th}$ edition (2000), the disclosure of which is specifically incorporated by reference herein, and is different from the at least one tacky film former soluble or dispersible in water and the at least one tacky film former soluble in oil discussed above.

In one embodiment, the at least one additional film former is chosen from polyvinylpyrrolidones. Polyvinylpyrrolidones are available from, for example, ISP in different viscosity grades under the tradename PVP-K. The additional film former(s) may be present in the composition in an amount ranging from 0.1% to 10% relative to the total weight of the composition. In another embodiment, the additional film former(s) may be present in the composition in an amount ranging from 1% to 5%, relative to the total weight of the composition.

The fibers useful in the present invention may be chosen from natural and synthetic fibers. Natural fibers include, but are not limited to, cotton, silk, wool, and other keratin fibers. Synthetic fibers include, but are not limited to, polyester, rayon, nylon and other polyamide fibers. The fibers may, for example, be present in the composition in an amount ranging from 0.5% to 10% relative to the total weight of the composition. In a further embodiment, the fibers are present in an amount ranging from 1% to 5% relative to the total weight of the composition. In one embodiment, the fibers may, for example, have an average length ranging from 0.5 mm to 4.0 mm, such as from 1.5 mm to 2.5 mm.

At least one pigment is also present in the compositions of the invention. A pigment should be understood to mean inorganic (mineral) or organic, white or colored, and coated or uncoated particles. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium. For example, these organic pigments may include D&C Red No. 7 Calcium Lake, D&C Red No. 21 Aluminum Lake, FD&C Yellow No. 5 Aluminum Lake, FD&C Blue No. 1 Aluminum Lake. The at least one pigment of the invention may be chosen from the above and any other pigment or treated pigment known in the cosmetic arts. The at least one pigment may also be chosen from pearling agents, such as, for example, mica, iron oxides, titanium dioxide and any other pearling agent known in the cosmetic arts. The inventive composition may contain at least one pigment in an amount ranging from 0.5% to 15% by weight relative to the total weight of the composition. In another embodiment, the at least one pigment may be present in an amount ranging from 1% to 12% by weight relative to the total weight of the composition.

The compositions of the present invention may also contain, for example, dispersion enhancing agents such as the polysaccharide resin KAMA®, available from KAMA International Corp., Duluth, Ga., or surfactants such as sorbitan sesquioleate. Dispersion enhancing agents are especially preferred in pigmented products in order to keep viscosity at a useful level.

It is also possible to add to the composition of the invention any additive customarily used in cosmetic compositions, such as, but not limited to thickening agents, preservatives, UV-screening agents, fillers, polymer resins, volatile solvents, and waxes.

In another embodiment of the present invention, the inventive composition is in the form of a oil-in-water emulsion. In such an embodiment, a tacky film former can, for example, be included in each of the aqueous and oil phases of the emulsion. Accordingly, in this embodiment of the invention, the aqueous phase of the water-in-oil emulsion contains the at least one tacky film former soluble or dispersible in water and the oil phase contains the at least one tacky film former soluble in oil.

The present invention also provides for a method for providing length and/or volume to eyelashes by applying to the eyelashes a composition as described above. In this embodiment, the tacky film formers may work together to help the fibers sufficiently adhere to the eyelashes so that they stay on throughout the day and so that if multiple coats of mascara are applied one on top of the other, the fibers remain on the lashes. When only one of the required tacky film formers is present, the adherence of the fibers on the lashes has been observed to lessen.

The invention will be illustrated by, but is not intended to be limited to, the following examples.

EXAMPLE 1

The following mascara composition was prepared:

| PHASE | Ingredient | w/w % |
|---|---|---|
| A | Waxes | 8.3 |
| | Emulsifiers | 3 |
| | PVP/Eicosene copolymer | 1.5 |
| | Hydrogenated Polyisobutene | 10 |
| B | Deionized water | 45.5 |
| | Gum/thickener | 0.2 |
| | Polyvinylpyrrolidone | 1 |
| | Humectant | 2 |
| | Hydrolyzed Corn Starch (KAMA) | 0.95 |
| | Base (Triethanolamine) | 1.5 |
| | Defoaming agent | 0.1 |
| | Sorbitan sesquioleate | 0.2 |
| B1 | Black iron oxide (pigment) | 6 |
| C | Rayon flock fiber | 3 |
| D | Acrylates copolymer | 10 |
| E | Water | 1 |
| | Preservatives | 1.7 |
| F | SD40 alcohol (ethanol) | 5 |

Procedure for Preparation
  (1) Phase A was heated to 85°–90° C. in a side vessel.
  (2) In a main vessel the gum/thickener of Phase B was added to the deionized water of Phase B, mixed well, and then heated to about 40°–45° C. The polyvinylpyrrolidone was then added and mixed until dispersed. This was followed by addition of the humectant. A lightning mixer was used to mix the water phase.
  (3) The water phase was then heated to about 60°–65° C. Then the KAMA, base, defoaming agent, and the sorbitan sesquioleate were added with mixing and mixed for about 5 minutes.
  (4) Next, the pigment was added to the water phase of the solution of (3) using a lightning mixer at 60°–65° C. The pigment was mixed in until uniform in the water phase.
  (5) The water phase with the pigment in it from step (4) was then transferred and homogenized for about 1 hour at 60°–65° C.
  (6) After homogenizing, the water phase of (5) was transferred to the sweep mixer and heated to about 85°–90° C. The fibers were added with mixing (at moderate speed) until uniform, maintaining the temperature at 85°–90° C.
  (7) While the water phase of step (6) was being mixed with the sweep mixer, the oil phase of step (1) was added in slowly and the mixture emulsified for about 20 minutes. The temperature of both phases before and during emulsification was 85°–90° C.

(8) The mixer speed was slowed and the batch was cooled to about 45°–50° C., at which point the acrylates copolymer of phase D was added very slowly.

(9) The water and preservatives of phase E were premixed until clear, then added to the batch at about 40° C. and mixed until uniform.

(10) The alcohol was added at about 30°–35° C. and mixed until incorporated.

(11) Cooling was stopped at about 30°–32° C.

Results

The prepared mascara composition was applied to eyelashes and found to increase their volume and length.

EXAMPLE 2

The following mascara composition was prepared:

| PHASE | Ingredient | w/w % |
|---|---|---|
| A | Waxes | 8.3 |
|   | Emulsifiers | 3 |
|   | PVP/Eicosene copolymer | 1.5 |
|   | Hydrogenated Polyisobutene | 10 |
| B | Deionized water | 40.5 |
|   | Gum/thickener | 0.2 |
|   | Polyvinylpyrrolidone | 1 |
|   | Humectant | 2 |
|   | Hydrolyzed Corn Starch (KAMA) | 0.95 |
|   | Base (Triethanolamine) | 1.5 |
|   | Defoaming agent | 0.1 |
|   | Sorbitan sesquioleate | 0.2 |
| B1 | Black iron oxide (pigment) | 6 |
| C | Rayon flock fiber | 3 |
| D | Polyvinyl acetate | 15 |
| E | Water | 1 |
|   | Preservatives | 1.7 |
| F | SD40 alcohol (ethanol) | 5 |

The same procedure for preparation was followed as in Example 1.

The prepared mascara composition was applied to eyelashes and found to increase their volume and length.

What is claimed is:

1. A cosmetic composition comprising:
   at least one tacky film former soluble or dispersible in water;
   at least one tacky film former soluble in oil chosen from hydrogenated polyisobutenes, adipic acid/diethylene glycol/glycerin crosspolymers, polyethylenes, and polyvinyl laurates;
   at least one pigment; and
   fibers.

2. A cosmetic composition according to claim 1, wherein said at least one tacky film former soluble or dispersible in water is chosen from polyvinyl alcohols, polyvinyl acetates, vinylpyrrolidone/acrylates/lauryl methacrylate copolymers, acrylates/$C_{1-2}$ succinates/hydroxyacrylates copolymers, PVP/DMAPA acrylates copolymers, cellulose acetate phthalate aqueous dispersions, and crosslinked poly (2-ethylhexyl acrylates).

3. A cosmetic composition according to claim 2, wherein said at least one tacky film former soluble or dispersible in water is chosen from acrylates copolymers and polyvinyl acetates.

4. A cosmetic composition according to claim 1, wherein said at least one tacky film former soluble or dispersible in water is present in the composition in an amount ranging from 0.5% to 25% relative to the total weight of the composition.

5. A cosmetic composition according to claim 4, wherein said at least one tacky film former soluble or dispersible in water is present in the composition in an amount ranging from 1% to 15%, relative to the total weight of the composition.

6. A cosmetic composition according to claim 5, wherein said at least one tacky film former soluble or dispersible in water is present in the composition in an amount ranging from 1% to 10%, relative to the total weight of the composition.

7. A cosmetic composition according to claim 1, wherein said at least one tacky film former soluble in oil is chosen from hydrogenated polyisobutenes.

8. A cosmetic composition according to claim 1, wherein said at least one tacky film former soluble in oil is present in the composition in an amount ranging from 0.5% to 30% relative to the total weight of the composition.

9. A cosmetic composition according to claim 8, wherein said at least one tacky film former soluble in oil is present in the composition in an amount ranging from 1% to 20% relative to the total weight of the composition.

10. A cosmetic composition according to claim 9, wherein said at least one tacky film former soluble in oil is present in the composition in an amount ranging from 1% to 15% relative to the total weight of the composition.

11. A cosmetic composition according to claim 1, further comprising at least one additional film former.

12. A cosmetic composition according to claim 11, wherein said at least one additional film former is chosen from polyvinylpyrrolidones.

13. A cosmetic composition according to claim 1, wherein said at least one additional film former is present in the composition in an amount ranging from 0.1% to 10% relative to the total weight of the composition.

14. A cosmetic composition according to claim 13, wherein said at least one additional film former is present in the composition in an amount ranging from 1% to 5% relative to the total weight of the composition.

15. A cosmetic composition according to claim 1, wherein said fibers are chosen from natural and synthetic fibers.

16. A cosmetic composition according to claim 15, wherein said natural fibers are chosen from cotton, silk, wool, and other keratin fibers.

17. A cosmetic composition according to claim 15, wherein said synthetic fibers are chosen from polyester, rayon, nylon and other polyamide fibers.

18. A cosmetic composition according to claim 15, wherein said fibers have an average length ranging from 0.5 mm to 4.0 mm.

19. A cosmetic composition according to claim 18, wherein said fibers have an average length ranging from 1.5 mm to 2.5 mm.

20. A cosmetic composition according to claim 1, wherein said fibers are present in the composition in an amount ranging from 0.5% to 10% relative to the total weight of the composition.

21. A cosmetic composition according to claim 20, wherein said fibers are present in the composition in an amount ranging from 1% to 5% relative to the total weight of the composition.

22. A cosmetic composition according to claim 1, wherein said at least one pigment is present in said composition in an amount ranging from 0.5% to 15% by weight relative to the total weight of the composition.

23. A cosmetic composition according to claim 1, further comprising at least one ingredient chosen from dispersion enhancing agents and surfactants.

24. A cosmetic composition according to claim 1, wherein said composition is in the form of a water-in-oil emulsion.

25. A cosmetic composition according to claim 23, wherein
said aqueous phase of said water-in-oil emulsion contains said at least one tacky film former soluble or dispersible in water and
said oil phase of said water-in-oil emulsion contains said at least one tacky film former soluble in oil.

26. A method for providing volume and/or length to eyelashes, said method comprising applying to the eyelashes a composition comprising
at least one tacky film former soluble or dispersible in water;
at least one tacky film former soluble in oil chosen from hydrogenated polyisobutenes, adipic acid/diethylene glycol/glycerin crosspolymers, polyethylenes, and polyvinyl laurates;
at least one pigment; and fibers.

27. A mascara composition comprising in said mascara composition
at least one tacky film former soluble or dispersible in water;
at least one tacky film former soluble in oil chosen from hydrogenated polyisobutenes, adipic acid/diethylene glycol/glycerin crosspolymers, polyethylenes, and polyvinyl laurates;
at least one pigment; and fibers.

28. A mascara composition according to claim 27, wherein said at least one tacky film former soluble or dispersible in water is chosen from polyvinyl alcohols, polyvinyl acetates, vinylpyrrolidone/acrylates/lauryl methacrylate copolymers, acrylates/$C_{1-2}$ succinates/hydroxyacrylates copolymers, PVP/DMAPA acrylates copolymers, cellulose acetate phthalate aqueous dispersions, and crosslinked poly (2-ethylhexyl acrylates).

29. A mascara composition according to claim 28, wherein said at least one tacky film former soluble or dispersible in water is chosen from acrylates copolymers and polyvinyl acetates.

30. A mascara composition according to claim 27, wherein said at least one tacky film former soluble or dispersible in water is present in the composition in an amount ranging from 0.5% to 25% relative to the total weight of the composition.

31. A mascara composition according to claim 30 wherein said at least one tacky film former soluble or dispersible in water is present in the composition in an amount ranging from 1% to 15%, relative to the total weight of the composition.

32. A mascara composition according to claim 31, wherein said at least one tacky film former soluble or dispersible in water is present in the composition in an amount ranging from 1% to 10%, relative to the total weight of the composition.

33. A mascara composition according to claim 27, wherein said at least one tacky film former soluble in oil is chosen from hydrogenated polyisobutenes.

34. A mascara composition according to claim 27, wherein said at least one tacky film former soluble in oil is present in the composition in an amount ranging from 0.5% to 30% relative to the total weight of the composition.

35. A mascara composition according to claim 34, wherein said at least one tacky film former soluble in oil is present in the composition in an amount ranging from 1% to 20% relative to the total weight of the composition.

36. A mascara composition according to claim 35, wherein said at least one tacky film former soluble in oil is present in the composition in an amount ranging from 1% to 15% relative to the total weight of the composition.

37. A mascara composition according to claim 27, further comprising at least one additional film former.

38. A mascara composition according to claim 37, wherein said at least one additional film former is chosen from polyvinylpyrrolidones.

39. A mascara composition according to claim 27, wherein said at least one additional film former is present in the composition in an amount ranging from 0.1% to 10% relative to the total weight of the composition.

40. A mascara composition according to claim 39, wherein said at least one additional film former is present in the composition in an amount ranging from 1% to 5% relative to the total weight of the composition.

41. A mascara composition according to claim 27, wherein said fibers are chosen from natural and synthetic fibers.

42. A mascara composition according to claim 41, wherein said natural fibers are chosen from cotton, silk, wool, and other keratin fibers.

43. A mascara composition according to claim 41, wherein said synthetic fibers are chosen from polyester, rayon, nylon and other polyamide fibers.

44. A mascara composition according to claim 41, wherein said fibers have an average length ranging from 0.5 mm to 4.0 mm.

45. A mascara composition according to claim 44, wherein said fibers have an average length ranging from 1.5 mm to 2.5 mm.

46. A mascara composition according to claim 27, wherein said fibers are present in the composition in an amount ranging from 0.5% to 10% relative to the total weight of the composition.

47. A mascara composition according to claim 46, wherein said fibers are present in the composition in an amount ranging from 1% to 5% relative to the total weight of the composition.

48. A mascara composition according to claim 27, wherein said at least one pigment is present in said composition in an amount ranging from 0.5% to 15% by weight relative to the total weight of the composition.

49. A mascara composition according to claim 27, further comprising at least one ingredient chosen from dispersion enhancing agents and surfactants.

50. A mascara composition according to claim 27, wherein said composition is in the form of a water-in-oil emulsion.

51. A mascara composition according to claim 50, wherein
said aqueous phase of said water-in-oil emulsion contains said at least one tacky film former soluble or dispersible in water and
said oil phase of said water-in-oil emulsion contains said at least one tacky film former soluble in oil.

* * * * *